(12) United States Patent
Dollomaja et al.

(10) Patent No.: US 12,324,674 B2
(45) Date of Patent: Jun. 10, 2025

(54) VOXELIZATION OF A 3D STRUCTURAL MEDICAL IMAGE OF A HUMAN'S BRAIN

(71) Applicant: DASSAULT SYSTEMES, Velizy Villacoublay (FR)

(72) Inventors: Borana Dollomaja, Marseille (AL); Remi Vuillemot, Paris (FR); Nicolas Gazeres, Velizy-Villacoublay (FR)

(73) Assignee: DASSAULT SYSTEMES, Velizy Villacoublay (FR)

( * ) Notice: Subject to any disclaimer, the term of this patent is extended or adjusted under 35 U.S.C. 154(b) by 374 days.

(21) Appl. No.: 17/865,735

(22) Filed: Jul. 15, 2022

(65) Prior Publication Data

US 2023/0024878 A1   Jan. 26, 2023

(30) Foreign Application Priority Data

Jul. 16, 2021   (EP) .................................... 21305997

(51) Int. Cl.
*A61B 5/00*   (2006.01)
*A61B 5/369*   (2021.01)

(52) U.S. Cl.
CPC ............ *A61B 5/4064* (2013.01); *A61B 5/369* (2021.01); *A61B 5/742* (2013.01)

(58) Field of Classification Search
CPC ....... A61B 5/4064; A61B 5/369; A61B 5/742; G16H 30/40; G16H 50/50; G06T 17/005; G06T 2210/36; G06T 2210/41; G06T 17/205; G06T 2200/00

See application file for complete search history.

(56) References Cited

U.S. PATENT DOCUMENTS

2007/0057945 A1   3/2007   Olson

FOREIGN PATENT DOCUMENTS

| CN | 104545897 | * | 4/2015 |
| WO | WO 2015/185911 | * | 12/2015 |

OTHER PUBLICATIONS

Michel et al., "EEG Source Imaging: A Practical Review of the Analysis Steps", Frontiers in Neurology (Year: 2019).*

(Continued)

*Primary Examiner* — Qian Yang
(74) *Attorney, Agent, or Firm* — Oblon, McClelland, Maier & Neustadt, L.L.P.

(57) ABSTRACT

A computer-implemented method for voxelizing a 3D structural medical image of a human's brain. The method including obtaining a 3D structural medical image of the human's brain, including a reference frame, generating a voxelized 3D structural medical image, obtaining parameters of at least one EEG electrode sensor and, for each EEG electrode sensor: a localization in the voxelized 3D structural medical image's reference frame, and a sensor detection distance, obtaining a regular 3D grid of voxels, and for each voxel of the 3D grid, iteratively subdividing the voxel while the distance between the voxel and the localization of any electrode sensor is smaller than or equal to the sensor detection distance and while a size of the voxel is greater than a predetermined length, each subdivided voxel joining a finite number of voxels of the voxelized 3D structural medical image.

20 Claims, 10 Drawing Sheets

(56) References Cited

OTHER PUBLICATIONS

Darvas et al., "Mapping human brain function with MEG and EEG: methods and validation", NeuroImage 23 (2004) S289-S299 (Year: 2004).*
Gavit et al., "A Multiresolution Framework to MEG/EEG Source Imaging", IEEE Transactions on Biomedical Engineering, vol. 48, No. 10, Oct. 2001 (Year: 2001).*
Machine translation for CN 104545897 (Year: 2014).*
Bellec et al.—"Identification of large-scale networks in the brain using fMRI", www.elsevier.com/locate/ynimg, NeuroImage 29(4) (2006) pp. 1231-1243.
Desikan et al.—"An automated labeling system for subdividing the human cerebral cortex on MRI scans into gyral based regions of interest", www.elsevier.com/locate/ynimg, NeuroImage 31(3), (2006) pp. 968-980.
Caune "Brain source localization using SEEG recordings", HAL Open science (143 pages), Jul. 2017.
Destrieux et al.—"Automatic parcellation of human cortical gyri and sulci using standard anatomical nomenclature", Neuroimage 2010, Oct. 15; 53(1), 30 pages.
Fisher et al.—"Operational classification of seizure types by the International League Against Epilepsy: Position Paper of the ILAE Commission for Classification and Terminology", 2017, ILAE Position Paper, Epilepsia 58(4), pp. 522-530.
Grech et al.—"Review on solving the inverse problem in EEG source analysis", Journal of NeuroEngineering and Rehabilitation, 5(1), published Nov. 7, 2008, 33 pages.
Hashemi et al.—"The Bayesian Virtual Epileptic Patient: A probabilistic framework designed to infer the spatial map of epileptogenicity in a personalized large-scale brain model of epilepsy spread" NeuroImage, Elsevier, 2020, 53 pages.
Jirsa et al.—"The Virtual Epileptic Patient: Individualized whole-brain models of epilepsy spread", NeuroImage, Elsevier, 2016, 145, pp. 377-388.
Kalisman et al.—"Deriving physical connectivity from neuronal morphology", 2003, Biological Cybernetics, 88(3), pp. 210-218.
Salvador et al.—"Neurophysiological Architecture of Functional Magnetic Resonance Images of Human Brain", Cerebral Cortex, 15(9), Sep. 2005, pp. 1332-1342.
Thevenaz et al.—"Image Interpolation and Resampling", Handbook of Medical Imaging, Processing and Analysis, 1(1), pp. 393-420.
Owen et al.—"A Gaussian Process Model of Human Electrocorticographic Data", Cerebral Cortex, vol. 30, No. 10, Sep. 3, 2020, pp. 1-13.
Frisken et al."Adaptively Sampled Distance Fields: A General Representation of Shape for Computer Graphics", Computer Graphics. Siggraph 2000 Conference Proceedings. New Orleans, LA, Jul. 23-28, 2000; [Computer Graphics Proceedings. SIGGRAPH], New York, NY : ACM, US, Jul. 1, 2000, pp. 249-254.
Kirk et al."Toblerone: Surface-Based Partial Volume Estimation", IEEE Transactions on Medical Imaging, vol. 39, No. 5, Nov. 5, 2019.
Blenkmann et al.—"iElectrodes: A Comprehensive Open-Source Toolbox for Depth and Subdural Grid Electrode Localization", Frontiers in NeuroInformatics, vol. 11, Mar. 2, 2017.
European Search Reported dated Jan. 17, 2022 issued in corresponding EP patent application No. 21305997.5 (citing documents AA and AV-AY).

* cited by examiner determining, among the voxels of the voxelized 3D structural medical image encompassed in the voxel of the 3D grid, if one or more voxels of the voxelized 3D structural medical image having no neighbor voxel of the voxelized 3D structural medical image, thereby each voxel forming a new volume added to the 3D grid ⟵ S70 determining, among the voxels of the voxelized 3D structural medical image encompassed in the voxel of the 3D grid, if at least two voxels of the voxelized 3D structural medical image are neighbors, thereby the at least two neighbor voxels forming a new volume added to the 3D grid ⟵ S80 removing the voxel of the 3D grid ⟵ S90

FIG. 3

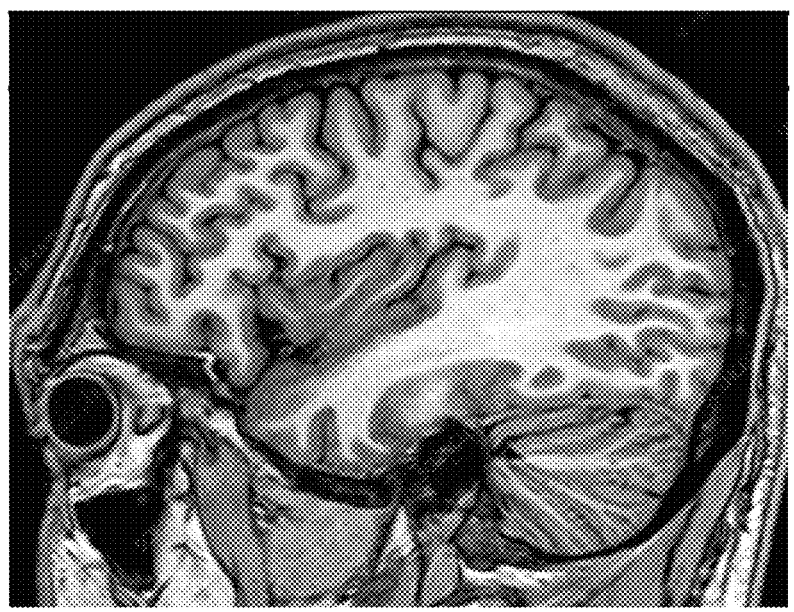
FIG. 4
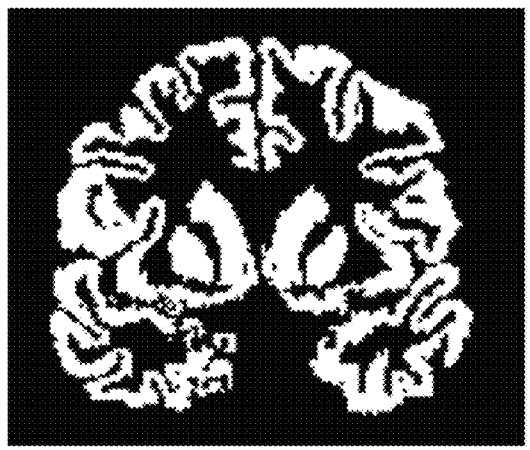 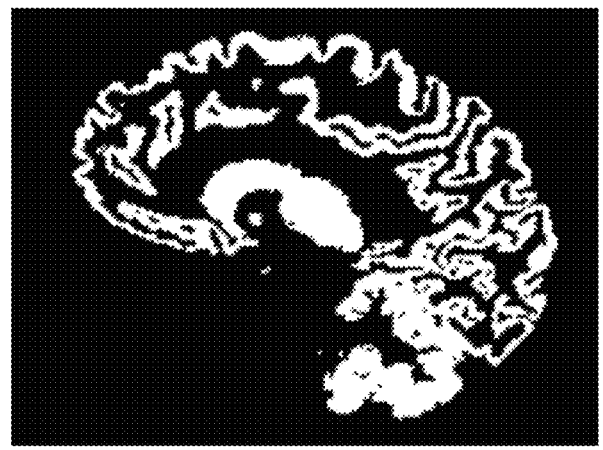
FIG. 5          FIG. 6

| Parcellation method | Number of regions | Computation time (seconds) | Epileptogenic zone volume (mm³) |
|---|---|---|---|
| Destrieux | 162 | 107 | 4269 |
| Uniform cubic | 2740 | 19643 | 1726 |
| Adaptive parcellation | 998 | 5106 | 2024 |

VOXELIZATION OF A 3D STRUCTURAL MEDICAL IMAGE OF A HUMAN'S BRAIN

FIELD

The disclosure relates to the field of computer programs and systems, and more specifically to a method, system and program for partitioning a 3D structural medical image of a human's brain.

BACKGROUND

Computer-implemented methods exist for partitioning a human's brain volume in a brain image. A brain image may be defined as a 3D image of the patient's brain structure. A brain image may be produced by a medical imaging device such as a computerized tomography (CT) scanner, an (Magnetic resonance imaging) MRI scanner, etc. It is typically exchanged as a data file in digital imaging and communications in medicine (DICOM) or neuroimaging informatics technology initiative (NIfTI) format.

Such methods may be, for example, useful for making use of electroencephalography (EEG) data, within a virtual brain. Indeed, methods for partitioning a human's brain volume in a brain image may be used for exploiting EEG data within a virtual brain to simulate the electrical activity within the virtual brain. These methods are especially used for making use of stereo-electroencephalography (SEEG) data.

A simulation of the electrical activity of a human's brain may be performed by using neural mass modeling. Neural mass modeling may be defined as an approach of modeling the brain activity where large regions, for example on the order of as much as one or more cubic centimeters ($cm^3$), of brain tissue are lumped to a single point in space and endowed with an equivalent electrical behavior. Neural mass modeling that lump an anatomical region to one single point in space, usually the region's center of gravity, have a drawback that the spatial relationship between the region's center of gravity and an electrode sensor gives an incomplete and biased account of the spatial relationship of the whole region to the sensor. To rephrase it, neural mass modeling assumes that the electrical activity of a region can be approximated by the electrical activity of one single point of the region. A region's center of gravity may be defined as the geometric center of the region if the region is considered of uniform density.

Traditionally, the methods for partitioning of a human's brain volume are based on standard anatomical atlases (e.g., Desikan R. S., Ségonne F., Fischl B., Quinn B. T., Dickerson, B. C., Blacker, D., Buckner R. L., Dale A. M., Maguire R. P., Hyman B. T., Albert, M. S. & Killiany R. J. (2006). An automated labeling system for subdividing the human cerebral cortex on MRI scans into gyral based regions of interest. *Neuroimage,* 31(3), 968-980; Destrieux, C., Fischl, B., Dale, A., & Halgren, E. (2010). Automatic parcellation of human cortical gyri and sulci using standard anatomical nomenclature. *Neuroimage,* 53(1), 1-15) and atlases derived thereof (e.g., Hashemi, M., Vattikonda, A. N., Sip, V., Guye, M., Bartolomei, F., Woodman, M. M., & Jirsa, V. K. (2020). The Bayesian Virtual Epileptic Patient: A probabilistic framework designed to infer the spatial map of epileptogenicity in a personalized large-scale brain model of epilepsy spread. *Neuroimage,* 217, 116839). An anatomical atlas may be defined as a generic partitioning of the brain in 3D. The partitioning is performed by an expert anatomist. An anatomical atlas divides the brain into anatomical regions, according to anatomical criteria (e.g., hemispheres, lobes, sulci, gyri . . . ). An anatomical atlas is built by averaging a number of individual brains and is meant to be of interest to analyze the brain of many individual humans, despite the variability that remains between the average brain and any particular human's brain. An anatomical region is a continuous portion of 3D space defined in an anatomical atlas. It represents a region of the brain, based on anatomical criteria only. Specifically, the definition of an anatomical atlas is not defined with respect to an electrode implantation.

These anatomically-based methods have one main advantage: the results of the partitioning can be easily understood by the clinicians because they are common-knowledge for the clinicians.

However, these anatomically based methods have many drawbacks when considering their use for simulating an electrical activity in a virtual brain, by using for example a neural mass modeling, the electrical activity being for example recorded with EEG or SEEG implantations. Indeed, these simulation algorithms assume a parcellation of the brain volume. The performance of the simulation algorithms (e.g., in terms of computation time and of precision of volume of the epileptogenic zone) may vary depending on the chosen parcellation. These variations of performance result from various elements resulting from the chosen parcellation.

First, the variation of performance is due to the inverse-problem problem in EEG or SEEG source analysis. The inverse problem appear when large anatomical regions are recorded from by more than one electrode sensor, which make the computation of a brain electrical activity of these regions from EEG or SEEG recordings an over-constrained problem (Grech R., Cassar T., Muscat J., Camilleri K. P., Fabri S. G., Zervakis M., Xanthopoulos P., Sakkalis V. & Vanrumste B. (2008). Review on solving the inverse problem in EEG source analysis. *Journal of neuroengineering and rehabilitation,* 5(1), 1-33).

Second, some anatomical regions are far away from any of the electrode sensors, thereby being unable to have any influence on any electrode sensor because of the attenuation over the distance in the brain tissue of the electrical signal. However, those distant regions are needed in the simulation of the electrical activity of the brain network and they bring a computational cost to the simulation. These anatomical regions, depending on the chosen parcellation, are small and in a great number, therefore involving a high computational cost to the simulation.

Third, these methods are used to estimate the location of an epileptogenic zone from the analysis of SEEG signals. They usually take a parcellation as input and express the epileptogenic zone as a combination of regions from the provided parcellation. An epileptogenic zone is defined as a brain area that, in some classes of epilepsy, is identified as a zone of defective brain tissue that is necessary and sufficient to trigger seizures. Ultimately, the epileptogenic zone may be the target of a surgery such as a resective surgery or a laser thermal ablation or ultrasound ablation. Consequently, its localization and extent must be well determined. Its extent must be large enough so that all the epileptogenic cortical tissue can be removed, but not too large so as to minimize the cognitive deficits entailed when removing safe brain tissue. The epileptogenic zone as determined from simulation algorithms is usually no smaller than the regions in the parcellation used as input. Hence, if the regions in the parcellation are large, like in anatomically based parcellation, then the epileptogenic zone built by additive combinations of these regions will be large too. It is worth noting that the SEEG electrodes are not placed randomly for recording the electrical activity of a patient's brain. Indeed, based on a diagnostic depending on the symptoms of the patient, a clinician will plan an adequate placement to optimize the localization of the epileptogenic zone.

Within this context, there is still a need for an improved method for voxelizing a 3D structural medical image of a human's brain.

SUMMARY

It is therefore provided a computer-implemented method for voxelizing a 3D structural medical image of a human's brain. Each voxel is suitable for running a simulator of an electrical activity of a 3D volume of the human's brain being enclosed by the voxel. The method comprises:
- providing a 3D structural medical image of the human's brain, the 3D structural medical image comprising a reference frame;
- generating a voxelized 3D structural medical image;
- providing parameters of at least one EEG electrode sensor and, for each EEG electrode sensor:
  - a localization in the voxelized 3D structural medical image's reference frame; and
  - a sensor detection distance;
- providing a 3D grid of voxels, each voxel of the 3D grid joining a same finite number of voxel(s) of the voxelized 3D structural medical image, the number of voxel(s) of the 3D grid being smaller than the number of voxels of the voxelized 3D structural medical image; and
- for each voxel of the 3D grid, iteratively subdividing the voxel while the distance between the voxel and the localization of any electrode sensor is smaller than or equal to the sensor detection distance and while a size of the voxel is greater than a predetermined length, each subdivided voxel joining a finite number of voxel(s) of the voxelized 3D structural medical image.

The method may comprise one or more of the following:
- the iteratively subdividing comprises: computing, for each voxel of the 3D grid a bounding sphere; computing, for each EEG electrode sensor, a sphere being centered at the EEG electrode sensor and a radius being equal to the sensor detection distance; determining, for each computed bounding sphere, if the computed bounding sphere is intersecting with the computed spheres; and for each voxel, subdividing the voxel if its computed bounding sphere is intersecting with one or more computed sphere while a size of the voxel is greater than the predetermined length, each subdivided voxel joining a finite number of voxel(s) of the voxelized 3D structural medical image;
- each voxel of the 3D grid having $2n$ voxels of the voxelized 3D structural medical image wherein $n \in \mathbb{N}$;
- removing the voxels of the voxelized 3D structural medical image that are not enclosing a brain grey matter in the voxelized 3D structural medical image;
- for each voxel of the 3D grid: determining, among the voxels of the voxelized 3D structural medical image encompassed in the voxel of the 3D grid, if one or more voxels of the voxelized 3D structural medical image having no neighbor voxel of the voxelized 3D structural medical image, thereby each voxel forming a new volume added to the 3D grid; determining, among the voxels of the voxelized 3D structural medical image encompassed in the voxel of the 3D grid, if at least two voxels of the voxelized 3D structural medical image are neighbors, thereby the at least two neighbor voxels forming a new volume added to the 3D grid; and removing the voxel of the 3D grid;
- for each volume of the 3D grid having less than a first predetermined minimum number of voxels of the voxelized 3D structural medical image, merging the volume with a neighbor volume of the 3D grid;
- for each volume of the 3D grid, discarding the volume having less than a second predetermined minimum number of voxels of the voxelized 3D structural medical image;
- the first and second predetermined minimum number of voxels rounding down a value representing 10% of the same finite number of voxel(s) of the voxelized 3D structural medical image;
- each generated voxel of the voxelized 3D structural medical image being cubic;
- all generated voxels of the voxelized 3D structural medical image having the same volume;
- each dimension of the voxelized 3D structural medical image having a same and even number of generated voxels;
- the sensor detection distance is between 10 and 100 millimeters, including 20 to 30 millimeters.

It is further provided a computer program comprising instructions for performing the method.

It is further provided a computer readable storage medium having recorded thereon the computer program.

It is further provided a database having recorded thereon the computer program.

It is further provided a system comprising a processor coupled to a memory, the memory having recorded thereon the computer program.

BRIEF DESCRIPTION OF THE DRAWINGS

Examples will now be described, by way of non-limiting example, and in reference to the accompanying drawings, where:

FIG. 3 shows a flowchart of an example of a post treatment compatible with the method;

FIG. 4 shows an example of a structural brain image;

FIG. 5 shows an example of a brain mask in a coronal plane;

FIG. 6 shows an example of a brain mask in a sagittal plane;

DETAILED DESCRIPTION

Figure 1:
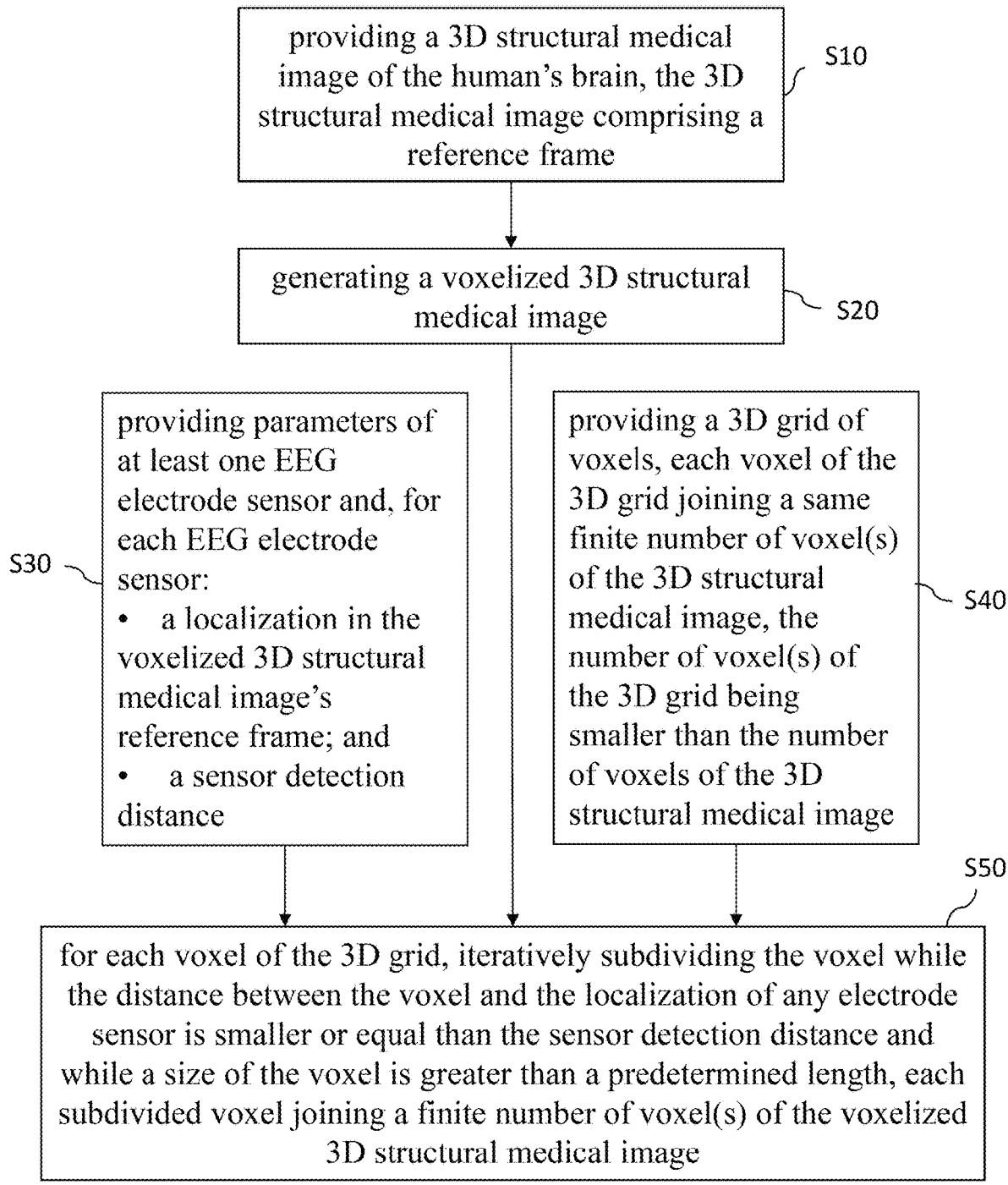
FIG. 1 shows a flowchart of an example of the method.

With reference to the flowchart of FIG. 1, it is proposed a computer-implemented method for voxelizing a 3D structural medical image of a human's brain. A voxelization is a partitioning, wherein each part of the partitioning is a voxel. Each voxel obtained by the method is suitable for running a simulator of an electrical activity of the 3D volume of the human's brain being enclosed by the voxel. The human's brain of the 3D structural medical image may be defined as a 3D volume representing the human's brain seen on the image. A voxel may be defined as a 3D shape having edges. As an example, a voxel may be a cuboid that is convex polyhedron bounded by six quadrilateral faces, whose polyhedral graph is the same as that of a cube.

The electrical activity of a 3D volume of a human's brain may be simulated. As an example, neural mass modeling is a well-known modeling and simulation technique in this domain. The simulated electrical activity may be endogenous (activity of brain cells) or exogenous (caused by externally applied electrical or magnetic stimulation). An electrical activity of a human's brain may be recorded by EEG electrode sensors (also referred to as EEG). EEG measures voltage fluctuations resulting from ionic current within the neurons of the brain. Clinically, EEG (i.e., scalp EEG) refers to the recording of the brain's spontaneous electrical activity over a period of time, as recorded from multiple electrodes placed on the scalp. An electrical activity of a human's brain may also be recorded by SEEG electrode sensors, and any other type of sensors adapted for recording electrical activity of a human brain. SEEG is the practice of recording electroencephalographic signals via depth electrodes, the electrodes being implanted into the brain tissue. SEEG may be used for patients with epilepsy not responding to medical treatment, and who are potential candidates to receive brain surgery in order to control seizures. An exogenous electrical activity in a human's brain may be created by a deep brain stimulation (DBS) electrode. A DBS electrode is an electrophysiological device implanted in the human's brain in order to send electrical impulses to specific target nuclei, deep inside the brain. An electrode (EEG, SEEG or DBS) may be defined as one sensor or an alignment of sensors. Each sensor may be made of platinum/iridium. It may have the shape of a cylinder about 2 millimeters long and 1 millimeter in diameter. An electrode may contain regularly, or non-regularly, spaced sensors. An electrode may contain more or less regularly spaced sensors. An electrode may comprise a set of sensors having identical parameters, e.g., the set may comprise at least one sensor or all the sensors of the electrode. A sensor may only detect the electrical activity of neurons in a restricted region of the brain around the sensor.

The method comprises providing S10 a 3D structural medical image of the human's brain. The 3D structural medical image comprises a reference frame. From now on, all orientations, directions and positions of all elements are computed in the 3D structural medical image's reference frame. FIG. 4 shows a brain image which may be used as a provided S10 3D structural medical image of the human's brain.

The method also comprises generating S20 a voxelized 3D structural medical image. The voxelization of the 3D structural medical image may be done by generating a 3D grid of voxels. Each voxel may contain an image intensity also known as grey level; being understood that image intensity might be represented by any other means, e.g., color scale. Each voxel may either be cubic (e.g., 1 millimeter (mm)×1 mm×1 mm) or may be a rectangular cuboid with different edge lengths along each dimension (e.g., 1.2 mm×1.2 mm×1.4 mm or 1.2 mm×1.4 mm×1.56 mm). The 3D grid may have the same number of voxels per dimension (e.g., 128×128×128 voxels), but for some 3D structural medical images, the number of voxels may be different along the three dimensions (for example, the grid could be 128×128×106 voxels, or 120×140×98 voxels). The voxelized 3D structural medical image comprises a reference frame. The reference frame of the voxelized 3D structural medical image may be the reference frame of the provided S10 3D structural medical image. Alternatively, the voxelized 3D structural medical image may have its own reference frame; in this case, every coordinate point in the reference frame of the voxelized 3D structural medical image can be transformed to a coordinate in the provided 3D structural medical image of the human's brain, or inversely. The step S20 consists in building a new equivalent 3D structural medical image, interpolating the provided S10 3D structural medical image on a grid of voxels. The generating S20 may be optional if the provided S10 3D structural medical image is already voxelized as the 3D structural medical image will directly be used as the voxelized 3D structural medical image.

The method also comprises providing S30 parameters of at least one EEG electrode sensor and, for each EEG electrode sensor, a localization in the voxelized 3D structural medical image's reference frame and a sensor detection distance. As an example, the parameters may comprise the size and the shape of the EEG electrode sensor. As said before, the parameters of the EEG electrode sensor (e.g., size and the shape) may be different for each EEG (or SEEG) electrode sensor depending for example on the brand and the model used. It is to be understood that the providing S30 might be performed for at least one SEEG electrode sensor parameters and/or at least one EEG electrode sensor parameters.

For each EEG electrode sensor, a localization in the voxelized 3D structural medical image's reference frame is provided. The localization may be provided as a position of the center of the electrode sensor in the reference frame of the generated S20 voxelized 3D structural medical image. It may also be provided as a position of the center of the electrode sensor in the reference frame of the provided S10 3D structural medical image. It may also be provided as a position of any point of the electrode sensor in the reference frame of the generated S20 voxelized 3D structural medical image or in the reference frame of the provided S10 3D structural medical image. For each EEG (or SEEG or DBS) electrode sensor, a sensor detection distance is provided. A sensor detection distance may be defined as the maximum distance an electrode sensor can detect the electrical activity of a human's brain from it. As an example, the sensor detection distance of a SEEG electrode sensor may be about 20 to 30 mm (Caune V. (2017). Brain source localization using SEEG recordings. Thesis, University of Lorraine, page 17).

The method also comprises providing S40 a 3D grid of voxels, each voxel of the 3D grid joining a same finite number of voxel(s) of the voxelized 3D structural medical image, the number of voxel(s) of the 3D grid being smaller than the number of voxel(s) of the voxelized 3D structural medical image. Joining a finite number of voxel(s) may be defined as connecting or performing the union of one or more entire voxels. Each voxel of the voxelized 3D structural medical image is entirely encompassed in a single voxel of the 3D grid. Furthermore, the voxel(s) of the voxelized 3D structural medical image encompassed in the same voxel of the 3D grid form a continuous set of voxels. To rephrase it, each voxel of the voxelized 3D structural medical image is a neighbor of one or more voxels of the voxelized 3D structural medical image encompassed in the same voxel of the 3D grid. A voxel is neighbor with another voxel if it shares with the another voxel either one or more edges and/or one or more vertices and is encompassed in the same voxel of the 3D grid than the another voxel. As an example, a voxel of the 3D grid may join (i.e., connect) 8, 64, 32768 or 262 144 voxels of the voxelized 3D structural medical image. The longest edge length of a voxel of the 3D grid may be defined as the longest edge length of the largest voxel of the 3D grid. As an example, it may be 8 millimeters, 16 millimeters, 32 millimeters or 64 millimeters. The 3D grid of voxels may also be generated, for example after step S20 or after step S30 or after step S40. The 3D grid may be generated by using the generated voxelized 3D structural medical image. For example, a voxel of the 3D grid may be the union of n continuous voxels of the generated voxelized 3D structural medical image, with $n \in \mathbb{N}$ and $n>1$. The union may comprise 2*2*2, 24*48*12 or 64*64*64 continuous voxels of the generated voxelized 3D structural medical image.

The method also comprises, for each voxel of the 3D grid, iteratively subdividing S50 the voxel of the provided 3D grid while the distance between the voxel and the localization of any electrode sensor is smaller or equal than the sensor detection distance and while a size of the voxel is greater than a predetermined length, each subdivided voxel joining a finite number of voxel(s) of the voxelized 3D structural medical image. In other words, depending on the distance of a voxel of the grid to the localization of any electrode sensor, the voxel can be subdivided into two or more voxels of the 3D grid. The subdivision ensures that each voxel obtained by the subdivision (i.e., subdivided voxel) does not intersect with any voxel of the voxelized 3D structural medical image. To rephrase it, a voxel of the voxelized 3D structural medical image cannot be divided by a voxel resulted from the subdivision S50.

The distance between the voxel and the localization of any electrode sensor may be computed in various ways. As an example, the distance between a sensor and a voxel of a grid may be computed between the center of any electrode sensor and any point of the considered voxel. In that case, as an example, the distance used may be equal to the sensor detection distance. As another example, the distance between a sensor and a voxel of a grid may be computed between the center of any electrode sensor and the center of a voxel of the 3D grid. In that case, as an example, the distanced used may be the sum of the sensor detection distance SDD plus the longest edge length e of the considered voxel multiplied by $\sqrt{3}/2$: $d=SDD+e*\sqrt{3}/2$. The subdivision is only possible for a considered voxel if the size of the voxel is greater or equal than a predetermined length. In other words, the iterative subdivision stops when the size of the subdivided voxel is smaller than the predetermined length. The size of the voxel may be the length of the smallest edge of the voxel. It may also be the length of the longest edge length or the mean edge length of all edges of the voxels. It may also be the longest line segment included in the considered voxel. The size of the voxel of the 3D grid may be also edited after step S20 or after step S30 or after step S40. The edition of the size of each voxel may be performed by the user by setting manually the length of each edge for each voxel of the 3D grid. The edition of the size of the voxels of the 3D grid may also be performed automatically by the system to all voxels based on predetermined user's preferences (e.g a predetermined length of all edges for all voxels of the 3D grid). As an example, for a cuboid, it may be the diagonal or the length of a predetermined edge.

For each voxel of the 3D grid, the distance is computed for each sensor. If one sensor is closer to the voxel than the sensor detection distance, the voxel will be subdivided. Then for each subdivided voxel, the distance is computed with all sensors and the considered voxel will be subdivided (again) if one sensor is closer to the voxel than the sensor detection distance and if the size of the voxel is greater than a predetermined length.

The predetermined length may be expressed as an integer multiple of the edge length of a voxel of the voxelized 3D structural medical image. As an example, the predetermined length may be 2 times or 4 times the edge length of a voxel of the voxelized 3D structural medical image. It may also be expressed in millimeters, for example, between 2 and 30 millimeters. As an example, the predetermined length may be greater than the length of the largest of the one or more sensors used. The predetermined length may also be greater than a minimal value required by the simulator of the electrical activity.

The predetermined length may also be determined by considering its impact on the computing resources during the simulation of the electrical activity. Indeed, the smaller the predetermined length, the longer the simulation may take.

As an example, each voxel of the grid may be subdivided in $2^n$ voxels with n within the range [1, 6]. Each voxel of the grid may be subdivided in 8 voxels (n=3).

Such a method improves the voxelization (or parcellation) of a 3D structural medical image of a human's brain. The voxels obtained with the present method are suitable for running a simulator of an electrical activity of the 3D volume of the human's brain being enclosed by the voxel; this means that each voxel obtained with the present method can be used (or will be used at a later stage) for the purpose of simulating an electrical activity of a 3D volume of a human's brain represented by and enclosed in the voxel in the provided 3D structural medical image of the human's brain. The parcellation, and thus the obtained voxels, improve the simulation of the electrical activity for at least the following reasons, being understood that simulation improvements are independent of the simulation method that is used, e.g., neural mass modeling is a well-known modeling and simulation technique in this domain.

First, the parcellation is built according to the locations of the sensors in an electrode implantation and is optimized for these locations. The method covers the whole brain territory: larger voxels provide gross representation of the brain far from the sensors, where the brain activity is too far and too attenuated by distance to be recorded by the sensor; smaller voxels provide more representation detail near the electrode sensors where the brain activity is more precisely recorded.

Second, when the parcellation is taken as input to simulate the electrical brain activity, the method helps reducing the number of electrode sensors per voxel of the 3D grid to make the inverse problem better posed. By reducing the over-constraining of the computation of a brain electrical activity of the voxel of the 3D grid from EEG SEEG or DBS recordings, the method will help reducing the computational cost of the simulation.

Third, as already mentioned, distant regions from any electrode sensors may be needed in the simulation of an electrical activity of the brain network. They bring a computational cost to the simulation, which is dependent on the number of distant regions needed. The method still take into account those needed distant regions but would represent them with coarser level of detail, so as to minimize their number and their associated computational cost.

Fourth, the method ensures that each region has a center of gravity, which is representative for the whole region for the simulation of its electrical activity. In other words, the method ensures that by simulating the electrical activity for the center of gravity of a voxel, the simulated activity will be representative of any point of the voxel.

Finally, the method, when used as input to simulation algorithms to estimate the location of an epileptogenic zone from the analysis of SEEG signals, may allow smaller epileptogenic zone than the anatomically based parcellation. To rephrase it, the method makes use of fine grained regions around the electrode implantation, therefore optimizing the epileptogenicity estimation, and the epileptogenic region may result from combining a number of smaller regions, yielding a less extended candidate region for surgery.

The method is computer-implemented. This means that steps (or substantially all the steps) of the method are executed by at least one computer, or any system alike. Thus, steps of the method are performed by the computer, possibly fully automatically, or, semi-automatically. In examples, the triggering of at least some of the steps of the method may be performed through user-computer interaction. The level of user-computer interaction required may depend on the level of automatism foreseen and put in balance with the need to implement user's wishes. In examples, this level may be user-defined and/or pre-defined.

A typical example of computer-implementation of a method is to perform the method with a system adapted for this purpose. The system may comprise a processor coupled to a memory and a graphical user interface (GUI), the memory having recorded thereon a computer program comprising instructions for performing the method. The memory may also store a database. The memory is any hardware adapted for such storage, possibly comprising several physical distinct parts (e.g., one for the program, and possibly one for the database).

Figures 15, 16:
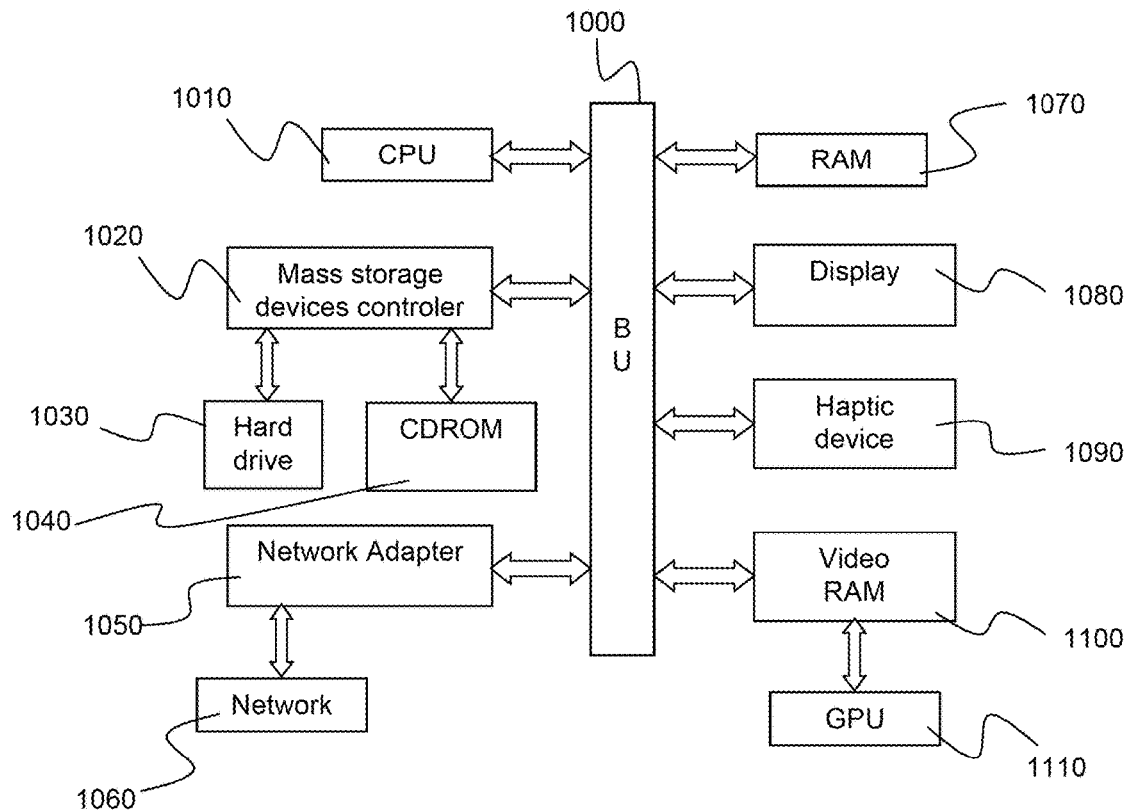
FIG. 15 shows an example of the system.
FIG. 16 shows an example of results, in terms of number of regions, computation time and epileptogenic zone volume, for three different parcellation methods.

FIG. 15 shows an example of the system, wherein the system is a client computer system, e.g., a workstation of a user.

The client computer of the example comprises a central processing unit (CPU) 1010 connected to an internal communication BUS 1000, a random access memory (RAM) 1070 also connected to the BUS. The client computer is further provided with a graphical processing unit (GPU) 1110 which is associated with a video random access memory 1100 connected to the BUS. Video RAM 1100 is also known in the art as frame buffer. A mass storage device controller 1020 manages accesses to a mass memory device, such as hard drive 1030. Mass memory devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks 1040. Any of the foregoing may be supplemented by, or incorporated in, specially designed ASICs (application-specific integrated circuits). A network adapter 1050 manages accesses to a network 1060. The client computer may also include a haptic device 1090 such as cursor control device, a keyboard or the like. A cursor control device is used in the client computer to permit the user to selectively position a cursor at any desired location on display 1080. In addition, the cursor control device allows the user to select various commands, and input control signals. The cursor control device includes a number of signal generation devices for input control signals to system. Typically, a cursor control device may be a mouse, the button of the mouse being used to generate the signals. Alternatively or additionally, the client computer system may comprise a sensitive pad, and/or a sensitive screen.

The computer program may comprise instructions executable by a computer, the instructions comprising means for causing the above system to perform the method. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the method.

Figure 2:
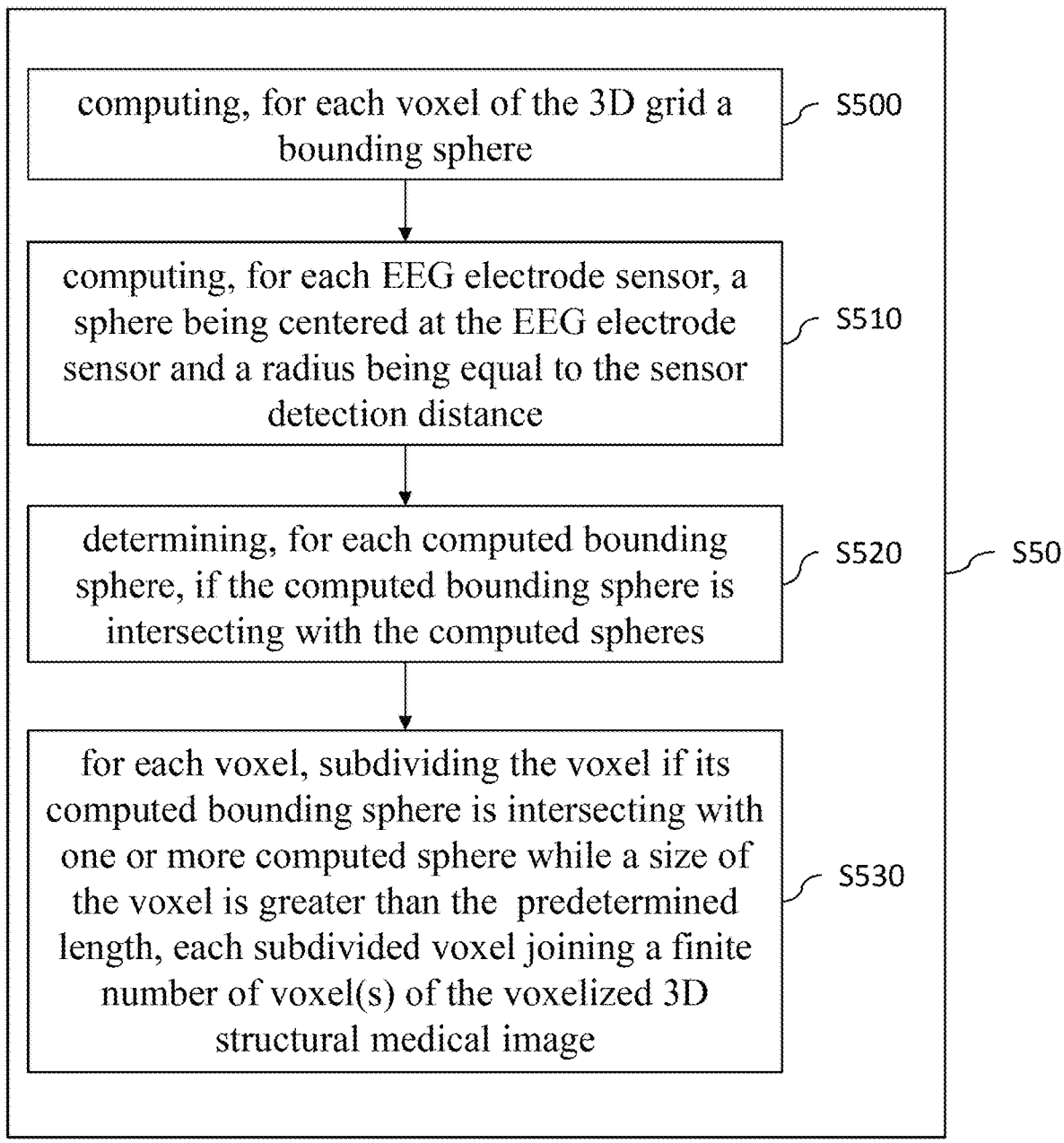
FIG. 2 shows a flowchart of an example of the iterative subdivision of each voxel of the 3D grid labelled at step S50 in FIG. 1.

An example of the iteratively subdividing S50 is now discussed in reference to FIG. 2. The iteratively subdividing S50 of the method may comprise computing S500, for each voxel of the 3D grid, a bounding sphere. A bounding sphere may be defined as a sphere enclosing the considered voxel. The bounding sphere is a special type of bounding volume. As an example, the bounding sphere may be the minimal bounding sphere, that is, the sphere with minimal radius among all bounding spheres. The bounding sphere may also have as a center the center of the considered voxel.

Still in reference to FIG. 2, the iteratively subdividing S50 of the method may further comprise computing S510, for each EEG electrode sensor, a sphere being centered at the EEG electrode sensor and a radius being equal to the sensor detection distance. The radius of the sphere may be different for each electrode sensor; the radius may depend on the one or more parameters of at least one EEG electrode sensor and/or the sensor detection distance. As mentioned earlier, the method is compatible with SEEG or DBS electrode sensor, the step S510 would be the same for SEEG or DBS electrode sensor as for EEG electrode sensor. It is worth noting that the computing 510 do not need to be done for each iteration. For example, the sphere may be computed and stored during the first loop and then be reused in the following loops.

Figure 7:
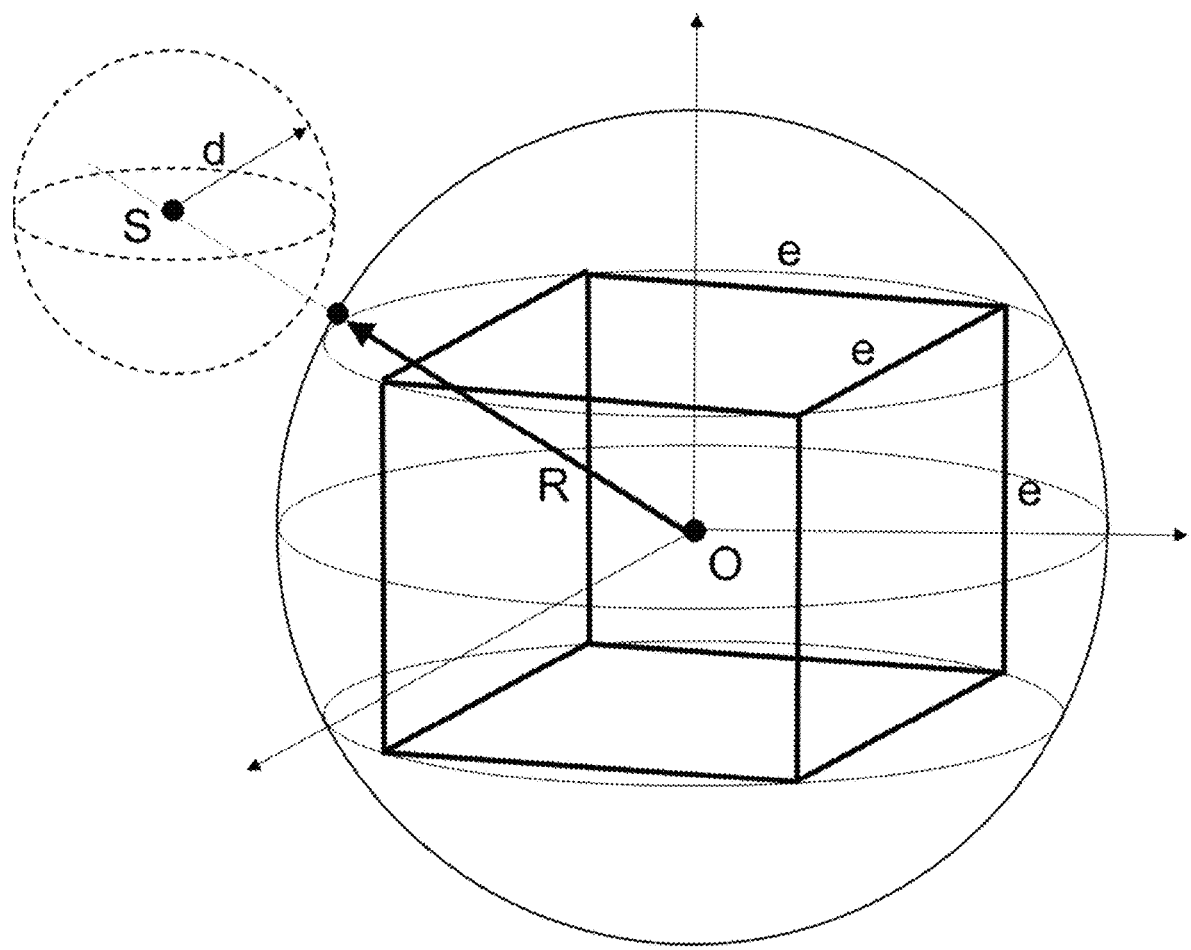
FIG. 7 shows an example of a distance criterion for computing a distance for the iterative subdivision of each voxel of the 3D grid.

Still in reference to FIG. 2, the iteratively subdividing S50 of the method may further comprise determining S520, for each computed bounding sphere of each voxel, if the computed bounding sphere is intersecting with the computed spheres of the EEG electrode sensor (S510) and, for each voxel, subdividing S530 the voxel if its computed bounding sphere is intersecting with one or more computed spheres of the EEG electrode sensor while the size of the voxel is greater than the predetermined length, each subdivided voxel joining a finite number of voxel(s) of the voxelized 3D structural medical image. Joining a finite number of voxel(s) may be defined as connecting or performing the union of one or more entire voxels. FIG. 7 illustrates this example of FIG. 2 of step S50.

As shown in FIG. 7, a sensor S has a computed sphere of radius d. For the sake of simplicity only, the considered voxel is cubic. The voxel has an edge length of e. As an example, the radius of its bounding sphere being R, with $R=\sqrt{3}/2*e$. Sensor S is considered to be able to detect the electrical activity that occurs inside the parcellation voxel whenever both spheres intersect, that is when $//OS// \leq R+d$. In FIG. 7, the computed bounding sphere is not intersecting with the computed sphere therefore the considered voxel may not be subdivided due to its distance to the sensor S.

Figure 8:
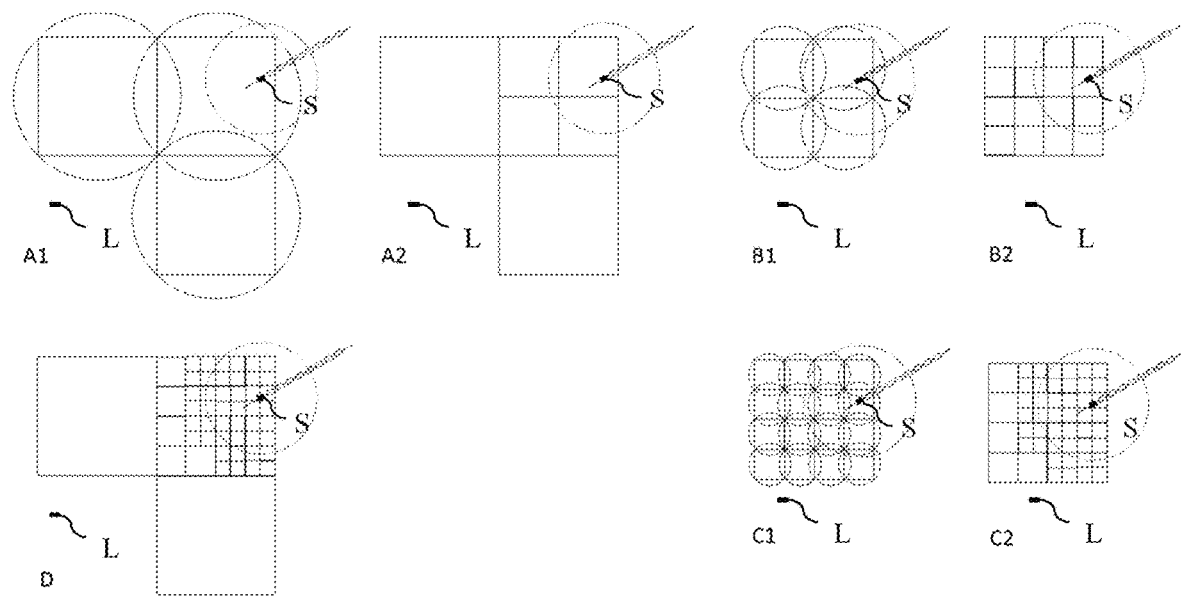
FIG. 8 shows an example, in 2D, of the iterative subdivision of each voxel of the 3D grid.

FIG. 8 shows an iterative subdivision S50 with a 2D view of a simplified example of 3 voxels of the 3D grid and one sensor S. For the sake of simplicity only, the voxelized 3D structural medical image is not represented. FIG. 8 shows the computed bounding sphere of each voxel drawn as a plain circle and the computed sphere of the sensor S is drawn as a dashed circle. Three iterations of the subdivision are shown. The first iteration is shown by FIGS. 8A1 and 8A2. The second iteration is shown by FIGS. 8B1 and 8B2. The third iteration is shown by FIGS. 8C1 and 8C2. The global result is shown in FIG. 8D. For each figure, a segment L has been added, the segment L representing the predetermined length used in step S530.

The FIG. A1 shows the steps S500, S510 and S520 for all 3 voxels and the sensor S. In step S520, only the computed bounding sphere of the top-right voxel is determined as intersecting with the computed sphere of the sensor S.

The FIG. 8A2 shows the step S530 for all 3 voxels. Only the top-right voxel is subdivided into 4 voxels.

The FIG. 8B1 shows the steps S500, S510 and S520 for the 4 voxels obtained by the subdivision shown in FIG. 8A2. In step S520, the computed bounding sphere of each of the 4 voxels intersects with the computed sphere of the sensor S and the size of the top right voxel is greater than the predetermined length L.

The FIG. 8B2 shows the step S530 for all 4 voxels. The 4 voxels are subdivided into 4 voxels each because the computed bounding sphere of the 4 voxels intersects with the computed sphere of the sensor S and the size of each of the 4 voxels is greater than the predetermined length L.

The FIG. 8C1 shows the steps S500, S510 and S520 for the 16 voxels obtained by the subdivision shown in FIG. 8B2. In step S520, the computed bounding sphere of 11 voxels intersects with the computed sphere of the sensor S.

The FIG. 8C2 shows the step S530 for all 16 voxels. The 11 voxels are subdivided into 4 voxels each because the computed bounding sphere of the 11 voxels intersects with the computed sphere of the sensor S and the size of each of the 11 voxels is greater than the predetermined length L.

After this iteration, 51 voxels are obtained as displayed in FIG. 8D. In FIGS. 8B and 8C, the largest 2 voxels are not displayed and it is worth noting that during the next iteration, none of the 51 voxels may be subdivided. Indeed, none of their computed bounding sphere intersects with the computed sphere of the sensor S, or their size is smaller than the predetermined length L.

As an example, when no voxel has been subdivided in the step S530 of the last iteration, the iterative subdivision S50 ends.

As another example, the iterative subdivision ends when the ratio between the size of the largest voxel of the 3D grid of voxels and the predetermined length exceeds a predetermined value, e.g., the predetermined value is input before starting the step S50. The upper round integer of the computed ratio is then used in a for-loop as the maximum number of iterations.

In FIG. 8D, we can see the result of the three iterations respectively shown by FIGS. 8A1 and 8A2, by FIGS. 8B1 and 8B2 and by FIGS. 8C1 and 8C2. Further iterations are not necessary because the computed bounding sphere of 7 voxels (the 7 biggest voxels shown in FIG. 8D) does not intersect with the computed sphere of the sensor S and the size of the other 44 voxels (the 44 smallest voxels shown in FIG. 8D) is smaller than the predetermined length. To rephrase it, further iterations would not change the result as none of the 51 voxels would be subdivided.

Such iterative subdivision S50, as discussed in reference to FIG. 2, improves the performance of the method in terms of computing resources. Indeed, by using a computed sphere for the sensor and a computed bounding sphere for each voxel of the 3D grid and each subdivided voxel, the method is optimized in terms of central process unit (CPU) usage. It is worth noting that step S500, S510, S520 and S530 may be computed in parallel. It may therefore processed across many threads on one or more cores of a CPU or a graphic process unit (GPU).

In examples, each voxel of the 3D grid may have $2^n$ voxels of the voxelized 3D structural medical image with n∈ $\mathbb{N}$. Here the terms "each voxel of the 3D grid" stands for "each voxel of the 3D grid before the iterative subdivision S50". For example, each voxel of the 3D grid may have the same number of voxels of the voxelized 3D structural medical image per dimension. In another example, each voxel of the 3D grid may have a different number of voxels of the voxelized 3D structural medical image per dimension. In other words, each voxel may have $2^n*2^n*2^n$ voxels with n∈ $\mathbb{N}$ or $2^p*2^q*2^r$ voxels with p, q and r E N. In another example, n, p, q and r may be greater than the maximum number of iterations possible in step S50.

By ensuring that each voxel of the 3D grid may have a power of two number of voxels of the voxelized 3D structural medical image per dimension, the method allows a fast and simple dichotomy for at least one dimension, and may be for each dimension. Furthermore, as long as n or the smallest number between p, q and r is greater than the number of iterations already done in step S50, no voxel of the voxelized 3D structural medical image may be divided by one of the subdivided voxel. In another example, each dimension may have a power of three (or five) number of voxels of the voxelized 3D structural medical image per dimension and the subdivision may be done respectively by three (or by five) for at least one dimension.

In examples, the method may further comprise removing S60 the voxels of the voxelized 3D structural medical image that are not enclosing a brain grey matter in the voxelized 3D structural medical image. A human brain comprises two main components: the grey matter and the white matter. The human brain's grey matter mainly occupies the outer layer of the brain and central subcortical structures. The grey matter is composed of neurons. The grey matter includes regions of the brain involved in muscle control, and sensory perception such as seeing and hearing, memory, emotions, speech, decision making, and self-control. White matter is composed of bundles, which connect various grey matter areas. White matter is the tissue through which messages pass between different areas of grey matter within the central nervous system. The brain grey matter may also be visualized directly in the provided S10 3D structural medical image. This is illustrated on FIGS. 5 and 6 that show an example of a brain mask respectively in a coronal and a sagittal plane. A brain mask is a brain image that only contains two kinds of voxels: those that represent brain (cortical or subcortical) grey matter and those that represent non-grey matter. Grey matter may be defined as representing the elements of neural computation in the brain. Non-grey matter may be defined as representing the rest of the brain (white matter, ventricles . . . ), non-brain parts of the head (eyes, throat, medulla, skull, skin . . . ) or the image background (outside of the head). In FIG. 5 and FIG. 6, the grey matter is represented in white color and the non-grey matter in black color.

The enclosed brain grey matter may be defined as a volume, or a 3D representation, on a 3D structural medical image representing the grey matter of the human's brain represented on the 3D structural medical image.

A voxel of the voxelized 3D structural medical image is considered as not enclosing a brain grey matter in the voxelized 3D structural medical image if none of the volume contained in the voxel is a brain grey matter. In other words, if a voxel contains even only partially brain grey matter, it will not be removed.

By removing S60 the voxels of the voxelized 3D structural medical image that are not enclosing a brain grey matter in the voxelized 3D structural medical image, the method is more efficient. Indeed, there is no need to compute electrical activity for voxels of the 3D grid joining only voxels of the voxelized 3D structural medical image that are not enclosing a brain grey matter in the voxelized 3D structural medical image. In other words, computation resources will be saved by removing S60 the voxels of the voxelized 3D structural medical image that are not enclosing a brain grey matter in the voxelized 3D structural medical image.

Figure 9:
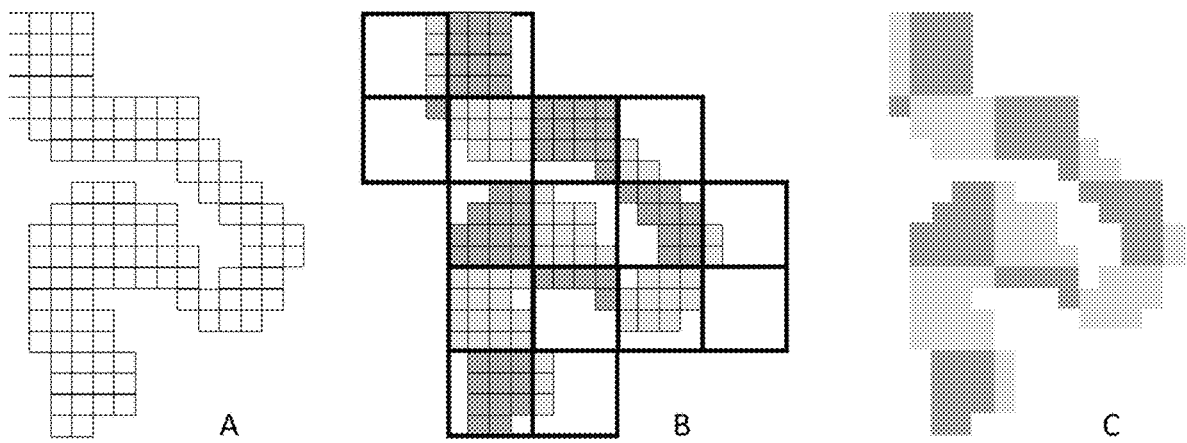
FIG. 9 and FIG. 10 show an example, in 2D, of volumes obtained with the method.
Figure 10:
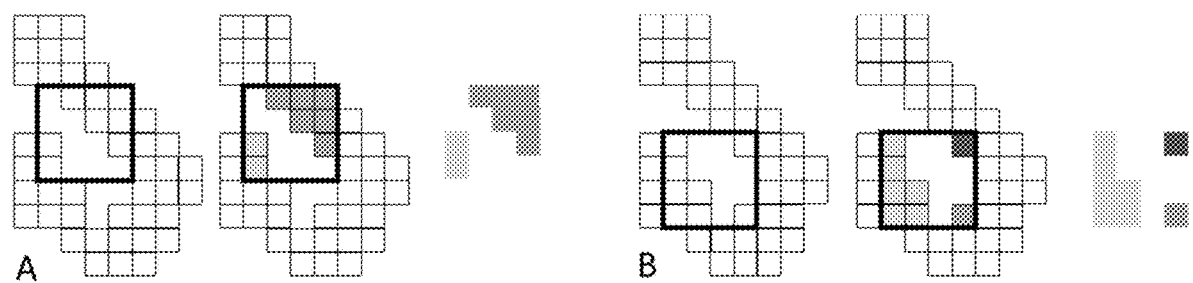

FIG. 9A shows an example of a voxelized 3D structural medical image wherein step S60 has been done. By removing S60 the voxels (of the voxelized 3D structural medical image) that are not enclosing a brain grey matter in the voxelized 3D structural medical image, each voxel of the 3D grid can be either completely void, partially void or entirely filled with voxels of the voxelized 3D structural medical image, as illustrated on FIG. 9B. FIG. 10 show another example of a voxelized 3D structural medical image wherein step S60 has been done.

In examples, illustrated by the flowchart of FIG. 3, the method may further comprise, for each voxel of the 3D grid, determining S70, among the voxels of the voxelized 3D structural medical image encompassed in the voxel of the 3D grid, if one or more voxels of the voxelized 3D structural medical image having no neighbor voxel of the voxelized 3D structural medical image, thereby each voxel forming a new volume added to the 3D grid. To rephrase it, in step S70, for each voxel of the 3D grid, if one or more voxels of the voxelized 3D structural medical image in the current voxel of the 3D grid is identified as isolated, a new volume per isolated voxel is created and added to the 3D grid. An isolated voxel may be defined as a voxel having no neighbor (i.e., does not touch either an edge or a corner of any other voxel) among the voxels encompassed in the same voxel of the 3D grid. The created volume added to the 3D grid will therefore be a duplicate of the isolated voxel.

After S70, and still for each voxel of the 3D grid, a determination S80 is carried out, among the voxels of the voxelized 3D structural medical image encompassed in the voxel of the 3D grid, for determining if at least two voxels of the voxelized 3D structural medical image are neighbors, thereby the at least two neighbor voxels forming a new volume added to the 3D grid. In step S80, when at least two voxels of the voxelized 3D structural medical image are neighbors, a new volume, constituted of the at least two voxels, is created and added to the grid.

Next, the voxel is removed of the 3D grid, leaving only the formed volumes.

The steps S80 and S90 may be done only if the volume to add to the 3D grid and the volume to remove to the 3D grid are not the same. In other words, if the considered voxel of the 3D grid is entirely filled with voxels of the voxelized 3D structural medical image encompassing a brain grey matter, the volume created in step S80 will be exactly the same than the voxel to remove in step S90, therefore by avoiding doing these two steps for this scenario, the steps S80 and S90 are carried out is more efficiently.

FIG. 9C shows an example of a result obtained after step S90. Each volume created and added to the 3D grid in step S70 and S80 are rendered either in a light grey color or in a dark grey color. FIGS. 10A and 10B show another example of a result obtained by performing step S70, S80 and S90 to one voxel of the 3D grid. In the left image of FIG. 10A and FIG. 10B, the small voxels (represented in 2D as squares) are voxels of the voxelized 3D structural medical image and the big voxel (represented in 2D as a larger and bold square) is a voxel of the 3D grid. In FIG. 10A, two volumes have been created from two sets of neighbor voxels in step S80. On the middle and right figure of the FIG. 10A, the two volumes are represented in two different grey shaded colors. In FIG. 10B, three volumes have been created from two isolated voxels in step S70 and one set of neighbor voxels in step S80. On the middle and right figure of the FIG. 10B, the three volumes are represented in three different grey shaded colors.

The steps S60, S70, S80 and S90 allow the method to take into consideration the divergence between the geometrical distance and the distance in term of brain grey matter between two voxels of the voxelized 3D structural medical image. The distance in term of brain grey matter is used to group the voxels of the voxelized 3D structural medical image and therefore to create a volume formed by one or more voxels of the voxelized 3D structural medical image. In other words, voxels of the voxelized 3D structural medical image can be joined in the same voxel of the 3D grid at step S40, but voxels of the voxelized 3D structural medical image can be no longer contiguous (i.e., forming a set of voxels wherein each voxel of the set is neighbor with at least one another voxel of the set) as a result of performing S60, S70, S80 and S90. These voxels of the voxelized 3D structural medical image can therefore be considered to represent different cortical tissues and the subsequent neural simulation should avoid lumping those voxels into the same dynamical neural mass model. Indeed, as distance increases between cortical neurons, correlation in their activity tends to decay rapidly, which is a reason to consider them as separate dynamical entities in the dynamic model (Kalisman N., Silberberg G., & Markram H. (2003). Deriving physical connectivity from neuronal morphology. *Biological cybernetics*, 88(3), 210-218; Salvador R., Suckling J., Coleman M. R., Pickard J. D., Menon D., & Bullmore E. (2005). Neurophysiological architecture of functional magnetic resonance images of human brain. *Cerebral cortex*, 15(9), 1332-1342; Bellec P., Perlbarg V., Jbabdi S., Pélégrini-Issac M., Anton J. L., Doyon J., & Benali H. (2006). Identification of large-scale networks in the brain using fMRI. *Neuroimage*, 29(4), 1231-1243). As an example, in FIG. 10A, without steps S60 to S90, all voxels of the voxelized 3D structural medical image which are encompassed in the voxel of the 3D grid would be considered as a single volume due to their geometrical proximity and therefore considered as one region for which the electrical activity may be approximated by the electrical activity of one single point of the region (including by one single point near the center of mass of the region). By performing steps S60 to S90, the same voxels of the voxelized 3D structural medical image which are encompassed in the voxel of the 3D grid are now divided into two volumes, each volume will therefore be considered as a region for which the electrical activity may be approximated by the electrical activity of one single point of the region.

In examples, the method may further comprise, for each volume of the 3D grid having less than a first predetermined minimum number of voxels of the voxelized 3D structural medical image, merging S100 the volume with a neighbor volume of the 3D grid. Here two volumes are neighbors if they share a common edge or vertex. The merging comprises replacing the two volumes by one volume constituted of the union of the two volumes.

In examples, the method may further comprise, for each volume of the 3D grid having less than a first predetermined minimum number of voxels of the voxelized 3D structural medical image, iteratively merging S100 the volume with a neighbor volume of the 3D grid. To be more precise, the merging or iterative merging may be applied to volumes which were not contained initially in the same voxel of the 3D grid.

By merging the neighbor volumes, the number of volumes obtained by the method is reduced and therefore computation resources during a potential simulation of the electrical activity may be reduced.

In examples, the method may further comprise, for each volume of the 3D grid, discarding S110 the volume having less than a second predetermined minimum number of voxels of the voxelized 3D structural medical image. The discarding S110 may be processed with or without a preceding merging S100. The discarding may consist of removing the potential one or more volumes comprising less than a second predetermined minimum number of voxels of the voxelized 3D structural medical image of the 3D grid. The discarding S110 ensures that each volume in the 3D grid contains a minimum number of voxels of the voxelized 3D structural medical image of the 3D grid. Therefore, it reduces the number of volumes obtained by the method by removing the smallest volumes from the 3D grid. It may reduce the computation resources during a potential simulation of the electrical activity.

Examples of the first and second predetermined minimum number of voxels are now discussed. In an example, the first and second predetermined minimum number of voxels rounding down a value may represent 10% of the same finite number of voxel(s) of the voxelized 3D structural medical image. As an example, for a voxel of the 3D grid containing 64 voxels of the voxelized 3D structural medical image, the first and second predetermined minimum number of voxels may be 6. In another example, the first and second predetermined minimum number of voxels may be different and/or comprised within a range of 1 to 50%, and including within a range of 5 to 20%.

In another example, the first and second predetermined minimum number of voxels may be the rounding up value representing a percentage of the same finite number of voxel(s) of the voxelized 3D structural medical image.

In another example, the first and second predetermined minimum number of voxels may be different per volume. Indeed, it may depend on the distance between the considered volume and the localization of any electrode sensor. As an example, the greater the distance between the considered volume and the localization of any electrode sensor is, the greater the first and/or second predetermined minimum number of voxels may be.

In another example, the method may use only the first predetermined minimum number of voxels. As an example, the first predetermined minimum number of voxels rounding down a value representing 10% of the same finite number of voxel(s) of the 3D structural medical image. Any other examples illustrated above could be used for the first predetermined minimum number of voxels alone.

In another example, the method may use only the second predetermined minimum number of voxels. As an example, the second predetermined minimum number of voxels rounding down a value representing 10% of the same finite number of voxel(s) of the 3D structural medical image. Any other examples illustrated above could be used for the second predetermined minimum number of voxels alone.

In examples, each generated voxel of the voxelized 3D structural medical image is cubic. To rephrase it, the voxelized 3D structural medical image generated in step S20 will contain only cubic voxels. When the voxels of the voxelized 3D structural medical image and/or of 3D structural medical image are not cubic, the image may be transformed into a new, equivalent, image with cubic voxels using classical interpolation algorithms (e.g., Thévenaz P., Blu T. & Unser M. (2000). Image interpolation and resampling. *Handbook of medical imaging, processing and analysis*, 1(1), 393-420). By generating S20 cubic voxels, the voxels of the 3D grid having the same number of voxels of the voxelized 3D structural image for each dimension may also be cubic too. Therefore, generating S20 cubic voxels may, for each considered voxel of 3D grid, minimize the distance between its center of gravity and any of its extremities. When considering the center of gravity of a cubic voxel of 3D grid to be used in a potential simulation of the electrical activity, by minimizing this distance, the method increases the reliability of the potential simulation. Furthermore, for a cubic voxel, the distance between its center of gravity and any of its extremities (i.e., its 8 corners) is the same.

In examples, all generated voxels of the voxelized 3D structural medical image may have the same volume. By generating S20 voxels of the same volume, the voxels of the 3D grid having the same number of voxels of the voxelized 3D structural image may have the same volume. In an example, the generated voxels are cubic and have the same volume. For this example, each considered voxel of 3D grid having the same number of voxels of the voxelized 3D structural image for each dimension, will also be cubic and having the same volume.

In examples, each dimension of the voxelized 3D structural medical image may have a same and even number of generated voxels. To ensure each dimension of the voxelized 3D structural medical image may have a same and even number of generated voxels, various solutions are possible. As an example, when a voxelized 3D structural medical image has different numbers of voxels along the three dimensions and/or not an even number of voxels along the three dimensions, it may be possible to embed the image into a larger grid of voxels, with the same and even number of voxels along the three dimensions. For example, a 128×128×106 grid may be embedded into a 128×128×128 grid and a 120×140×98 grid may be embedded into a 256×256×256 grid. It may also be possible to reduce the number of voxels of one, two or even the three dimensions. In this example, it is important that no voxel encompassing a human's brain volume be removed. For example, a 128×128×136 grid may be embedded into a 128×128×128 grid and a 500×340×298 grid may be embedded into a 256×256×256 grid. In an example, the voxelized 3D structural medical image may have a same and a power of two number of cubic voxels along the three dimensions. This example allows a fast and simple dichotomy along the three dimensions. When both voxel resizing and grid resizing are needed, voxels may be first made cubic and then the number of voxels may be modified.

In examples, the sensor detection distance may be between 10 and 100 millimeters, including to 20 to 30 millimeters. The sensor detection distance may be different per sensor. Indeed, the sensor detection distance reflects the capacity of a sensor to detect the electrical brain activity at a certain distance from it.

The method may also be used in a pipeline dedicated to the estimation of the location of an epileptogenic zone from the analysis of SEEG signals (Jirsa V. K., Proix T., Perdikis D., Woodman M. M., Wang H., Gonzalez-Martinez J., Bernard C., Bénar C., Guye M., Chauvel P. & Bartolomei F. (2017). *The virtual epileptic patient: individualized whole-brain models of epilepsy spread. Neuroimage*, 145, 377-388). Indeed, such estimation is made by simulation algorithms, which take a parcellation as input and express the epileptogenic zone as a combination of regions from the provided parcellation. The disclosure is therefore of interest since combining smaller voxels obtained with our method can yield smaller and better-defined epileptogenic zones than with standard anatomical parcellations. As an example, the smallest voxels in the parcellation obtained by the method may be either 8 mm3 or 64 mm3. As a comparison, the smallest region size in standard anatomical parcellations is about 338 mm3 when based on the anatomical atlas of Destrieux et al. (2010) or 501 mm3 when based on the anatomical atlas of Desikan et al. (2006).

Figure 11:
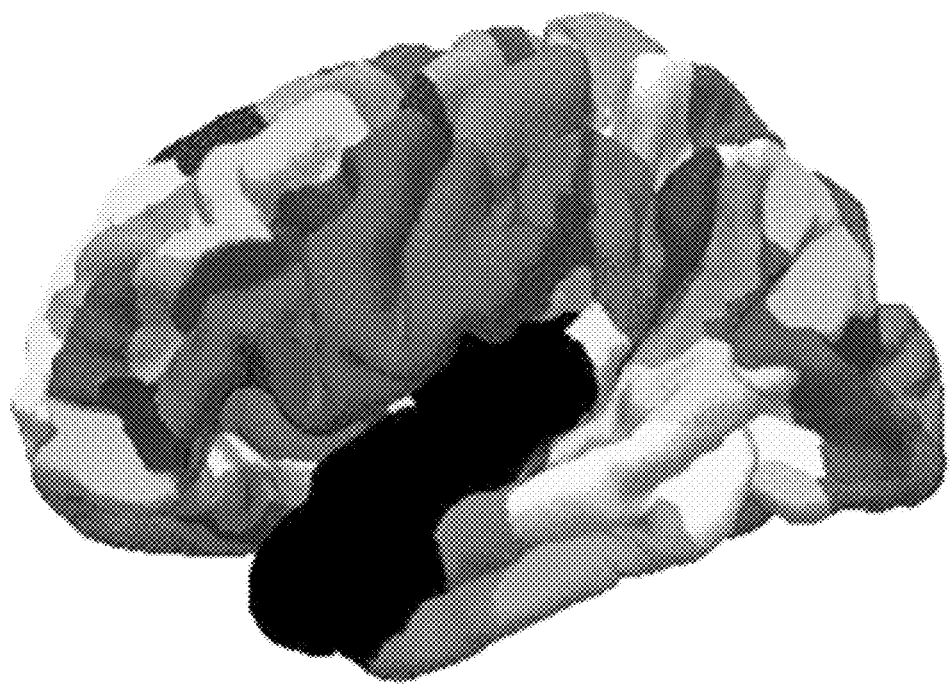
FIG. 11 shows an example of an anatomically based parcellation known in the art.

FIG. 11 shows an anatomically based parcellation according to the standard anatomical atlas of Destrieux et al. (2010). It is worth to remind that the parcellation is totally independent of the location of the electrode sensors.

Figure 12:
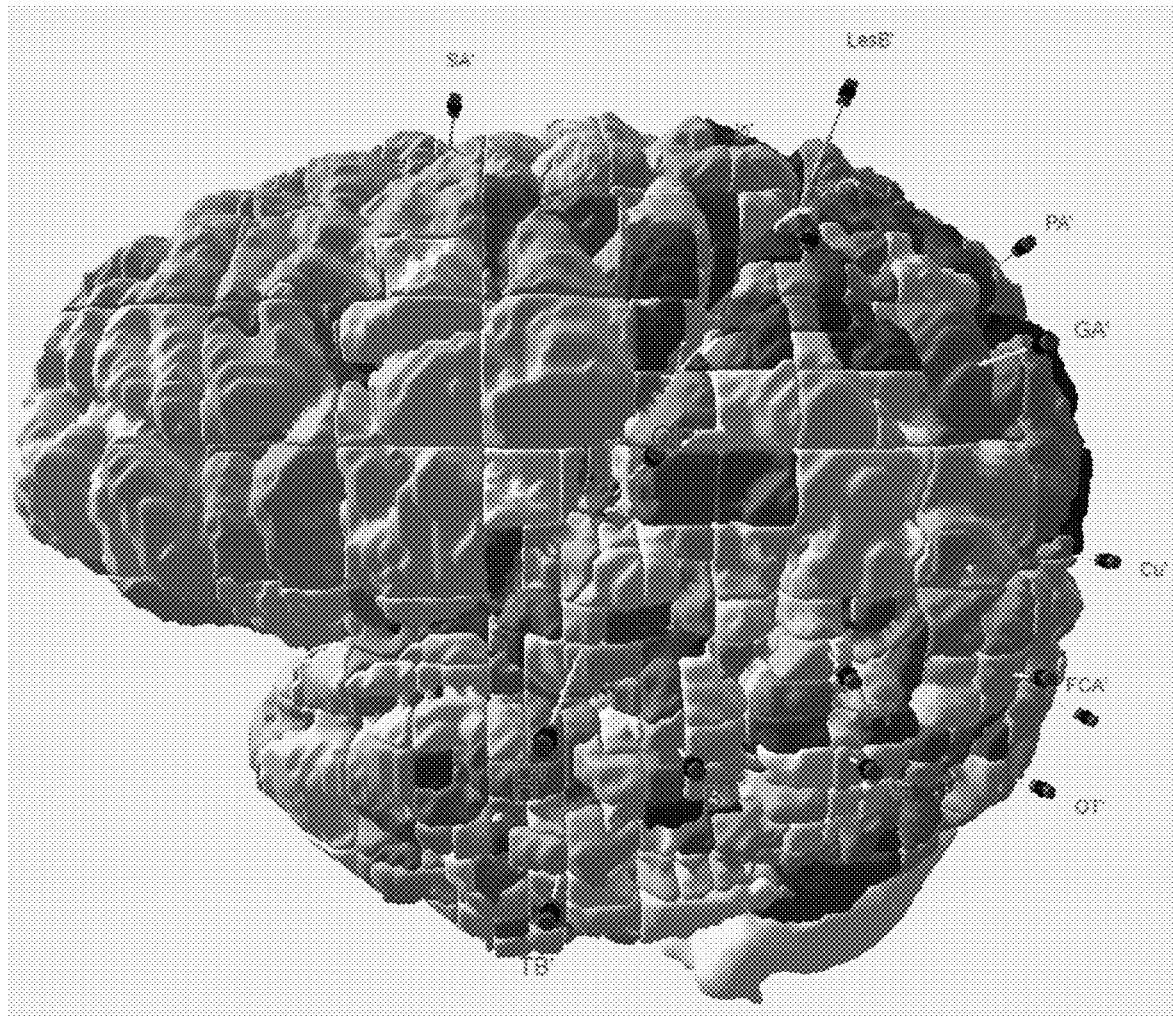
FIG. 12 shows an example of a parcellation obtained by the method.

FIG. 12 shows an example of a parcellation obtained by the method detailed above. This example of parcellation is specific to the location of the electrode sensors shown on FIG. 12.

Figure 13:
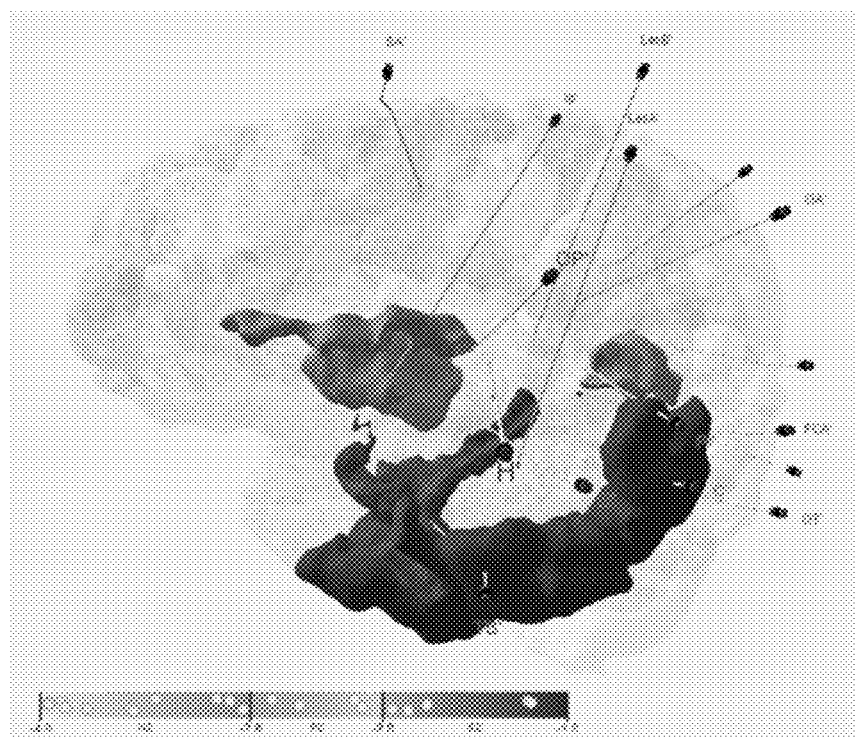
FIG. 13 shows an example of an estimated epileptogenic zone obtained with a simulation algorithm taking as input anatomically based parcellation know in the art.
Figure 14:
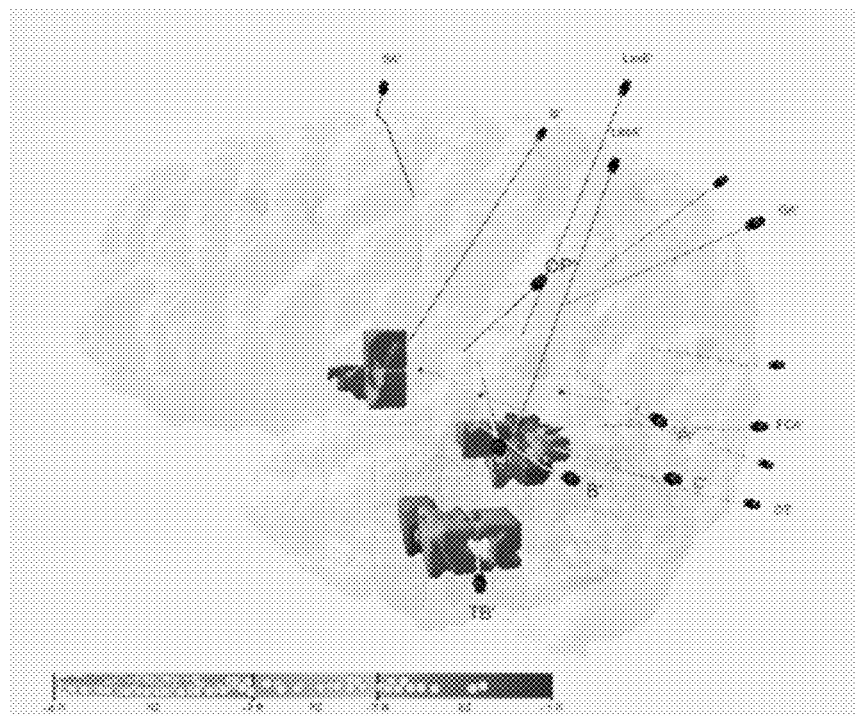
FIG. 14 shows an example of an estimated epileptogenic zone obtained with the same simulation algorithm taking as input a parcellation obtained with the method.

FIG. 13 shows an example of an estimated epileptogenic zone obtained with a simulation algorithm taking as input a parcellation based on the standard anatomical atlas of Destrieux et al. (2010). In this example, the simulation comprises fitting a neurodynamic brain model to recordings of the patient's electrical activity during an epileptic seizure. The neurodynamic brain model is a model with parameters, and any type of dynamic trajectory (i.e., any type of electrical activity) can be simulated by the model. The simulation algorithm further comprises finding the parameters of the neurodynamic brain model for which the electrical activity simulated by the model is the closest to the recordings of the epileptic activity recorded during the epileptic seizure of the patient. FIG. 14 shows an example of an estimated epileptogenic zone obtained with the same simulation algorithm taking as input a parcellation obtained with the method. For each figure, a scale representing the degree of epileptogenic of each region is displayed. The epileptogenicity value for each region is indicated as a circle on this scale. Epileptogenic zones are the regions with a dimensionless epileptogenicity value (the value is a dimensionless quantity obtained from a dimensionless model) greater than −2.0 (Jirsa, V. K., Proix, T., Perdikis, D., Woodman, M. M., Wang, H., Gonzalez-Martinez, J., Bernard, C., Bénard, C., Guye, M., Chauvel, P. & Bartolomei, F. (2017). The virtual epileptic patient: individualized whole-brain models of epilepsy spread. *Neuroimage*, 145, 377-388).

FIG. 16 shows an example of results, for the three different parcellation methods, in terms of:
   number of regions;
   computation time of a simulation algorithm taking as input a parcellation and outputting an estimation of the location of an epileptogenic zone from the analysis of SEEG signals; and
   volume of the estimated epileptogenic zone with the simulation algorithm.

The three parcellation methods are used as an input to the same simulation algorithm, which take a parcellation as input and express the estimated epileptogenic zone as a combination of regions from the provided parcellation. The simulation algorithm uses three times the same set of SEEG recordings and the only difference between the three runs was the parcellation method used.

The first method "Destrieux" concerns an anatomically based parcellation according to the standard anatomical atlas of Destrieux et al. (2010).

The second method "Uniform cubic" concerns a parcellation method tested by the applicant. It consists in having a parcellation with uniform cubic voxels of 8 mm³. In other words, a voxelized 3D structural medical image is generated from a provided a 3D structural medical image of the human's brain. Each voxel generated being cubic and having an edge length of 2 mm. Then the voxels of the voxelized 3D structural medical image that are not enclosing a brain grey matter in the voxelized 3D structural medical image have been removed.

The third method "adaptive parcellation" is the method according to an example.

In term of number of regions created, the first method "Destrieux" has 162 regions. These regions are independent of the size of the provided 3D structural medical image of the human's brain and the localization of the sensors in the voxelized 3D structural medical image's reference frame. The method "uniform cubic" has generated 2740 regions, this number is dependent on the size of the provided 3D structural medical image of the human's brain. The method "adaptive parcellation" produced 998 regions, this number is dependent on the size of the provided 3D structural medical image of the human's brain and the localization of the sensors in the voxelized 3D structural medical image's reference frame.

Regarding the computation resources, the result shown is the computation time of the simulation algorithm, the simulation algorithm being run on the same computer for the three runs. The method "Destrieux" is the fastest with a result obtained in 107 seconds. The method "Uniform cubic" is the slowest with a result obtained in 19643 seconds. The method "adaptive parcellation" has a computation time of 5106 seconds. Here the computation time of the simulation algorithm is dependent on the number of regions produced by the methods "Destrieux", "uniform cubic" or "adaptive parcellation". Indeed, the simulation algorithm simulates the electrical activity for each region.

Considering the column called "epileptogenic zone volume (mm³)", the result shown for each method is the volume of the computed epileptogenic zone by the simulation algorithm. The method "Uniform cubic" gives the smallest volume with 1726 cubic millimeters (mm³). The method "Adaptive parcellation" gives a volume of 2024 mm³ and the method "Destrieux" a volume of 4269 mm³.

To summarize, the method "Adaptive parcellation" used as an input for a simulation algorithm allows a computation around four times faster than for the method "cubic uniform" with an increase of around 17% of the volume of the epileptogenic zone compared to this method. Compared to the known parcellation called "Destrieux", even if the method has a computation time around 47 times greater than for the method "Destrieux", the computed volume of the epileptogenic zone with our method is 52% smaller.

It is to be understood that any combination of the examples of the method are possible.

The invention claimed is:

1. A computer-implemented method for voxelizing a 3D structural medical image of a human's brain, each voxel being suitable for running a simulator of an electrical activity of a 3D volume of the human's brain being enclosed by the voxel, the method comprising:
   obtaining a 3D structural medical image of the human's brain, the 3D structural medical image comprising a reference frame, wherein the 3D structural image stems from acquisition by a medical imaging device;
   generating a voxelized 3D structural medical image;
   obtaining parameters of at least one EEG electrode sensor and, for each EEG electrode sensor:
      a localization in a reference frame of the voxelized 3D structural medical image, and
      a sensor detection distance;
   obtaining a 3D grid of voxels, each voxel of the 3D grid joining a same finite number of voxels of the voxelized 3D structural medical image, the number of voxels of the 3D grid being smaller than the number of voxels of the voxelized 3D structural medical image; and
   for each voxel of the 3D grid, iteratively subdividing the voxel while the distance between the voxel and localization of any electrode sensor is smaller than or equal to the sensor detection distance and while a size of the voxel is greater than a predetermined length, each subdivided voxel joining a finite number of voxels of the voxelized 3D structural medical image.

2. The computer-implemented method of claim 1, wherein the iteratively subdividing further comprises:
   computing for each voxel of the 3D grid a bounding sphere;
   computing for each EEG electrode sensor, a sphere being centered at the EEG electrode sensor and a radius being equal to the sensor detection distance;
   determining, for each computed bounding sphere, when the computed bounding sphere is intersecting with the computed spheres; and
   for each voxel, subdividing the voxel when the respective computed bounding sphere is intersecting with one or more computed sphere while a size of the voxel is greater than the predetermined length, each subdivided voxel joining a finite number of voxels of the voxelized 3D structural medical image.

3. The computer-implemented method of claim 1, wherein each voxel of the 3D grid having 2n voxels of the voxelized 3D structural medical image wherein $n \in \mathbb{N}$.

4. The computer-implemented method according to claim 1, further comprising removing the voxels of the voxelized 3D structural medical image that are not enclosing a brain grey matter in the voxelized 3D structural medical image.

5. The computer-implemented method of claim 4, further comprising, for each voxel of the 3D grid:
   determining, among the voxels of the voxelized 3D structural medical image encompassed in the voxel of the 3D grid, when one or more voxels of the voxelized 3D structural medical image having no neighbor voxel of the voxelized 3D structural medical image, thereby each voxel forming a new volume added to the 3D grid;
   determining, among the voxels of the voxelized 3D structural medical image encompassed in the voxel of the 3D grid, whether at least two voxels of the voxelized 3D structural medical image are neighbors, thereby the at least two neighbor voxels forming a new volume added to the 3D grid; and
   removing the voxel of the 3D grid.

6. The computer-implemented method of claim 5, further comprising, for each volume of the 3D grid having less than a first predetermined minimum number of voxels of the voxelized 3D structural medical image, merging the volume with a neighbor volume of the 3D grid.

7. The computer-implemented method of claim 5, further comprising, for each volume of the 3D grid, discarding the volume having less than a second predetermined minimum number of voxels of the voxelized 3D structural medical image.

8. The computer-implemented method of claim 7, wherein the first and second predetermined minimum number of voxels rounding down a value representing 10% of a same finite number of voxels of the voxelized 3D structural medical image.

9. The computer-implemented method according to claim 1, wherein each generated voxel of the voxelized 3D structural medical image being cubic.

10. The computer-implemented method according to claim 1, wherein all generated voxels of the voxelized 3D structural medical image having the same volume.

11. The computer-implemented method according to claim 1, wherein each dimension of the voxelized 3D structural medical image has a same and even number of generated voxels.

12. The computer-implemented method according to claim 1, wherein the sensor detection distance is between 20 to 30 millimeters.

13. A non-transitory computer readable storage medium having recorded thereon a computer program having instructions for performing a method for voxelizing a 3D structural medical image of a human's brain, each voxel being suitable for running a simulator of an electrical activity of a 3D volume of the human's brain being enclosed by the voxel, the method comprising:
   obtaining a 3D structural medical image of the human's brain, the 3D structural medical image comprising a reference frame, wherein the 3D structural image stems from acquisition by a medical imaging device;
   generating a voxelized 3D structural medical image;

obtaining parameters of at least one EEG electrode sensor and, for each EEG electrode sensor:
a localization in a reference frame of the voxelized 3D structural medical image, and
a sensor detection distance;
obtaining a 3D grid of voxels, each voxel of the 3D grid joining a same finite number of voxels of the voxelized 3D structural medical image, the number of voxels of the 3D grid being smaller than the number of voxels of the voxelized 3D structural medical image; and
for each voxel of the 3D grid, iteratively subdividing the voxel while the distance between the voxel and localization of any electrode sensor is smaller than or equal to the sensor detection distance and while a size of the voxel is greater than a predetermined length, each subdivided voxel joining a finite number of voxel(s) of the voxelized 3D structural medical image.

14. The non-transitory computer readable storage medium of claim 13, wherein the iteratively subdividing comprises:
computing for each voxel of the 3D grid a bounding sphere;
computing for each EEG electrode sensor, a sphere being centered at the EEG electrode sensor and a radius being equal to the sensor detection distance;
determining, for each computed bounding sphere, when the computed bounding sphere is intersecting with the computed spheres; and
for each voxel, subdividing the voxel when the computed bounding sphere is intersecting with one or more computed sphere while a size of the voxel is greater than the predetermined length, each subdivided voxel joining a finite number of voxels of the voxelized 3D structural medical image.

15. The non-transitory computer readable storage medium of claim 13, wherein each voxel of the 3D grid having 2n voxels of the voxelized 3D structural medical image wherein $n \in \mathbb{N}$.

16. The non-transitory computer readable storage medium of claim 13, wherein the method further comprises removing the voxels of the voxelized 3D structural medical image that are not enclosing a brain grey matter in the voxelized 3D structural medical image.

17. An apparatus comprising:
a processor; and
a database having a non-transitory computer readable storage medium having recorded thereon a computer program having instructions for voxelizing a 3D structural medical image of a human's brain, each voxel being suitable for running a simulator of an electrical activity of a 3D volume of the human's brain being enclosed by the voxel that when executed by the processor causes the processor to be configured to:
obtain a 3D structural medical image of the human's brain, the 3D structural medical image comprising a reference frame, wherein the 3D structural image stems from acquisition by a medical imaging device;
generate a voxelized 3D structural medical image;
obtain parameters of at least one EEG electrode sensor and, for each EEG electrode sensor:
a localization in a reference frame of the voxelized 3D structural medical image, and
a sensor detection distance;
obtain a 3D grid of voxels, each voxel of the 3D grid joining a same finite number of voxels of the voxelized 3D structural medical image, the number of voxels of the 3D grid being smaller than the number of voxels of the voxelized 3D structural medical image; and
for each voxel of the 3D grid, iteratively subdivide the voxel while the distance between the voxel and localization of any electrode sensor is smaller than or equal to the sensor detection distance and while a size of the voxel is greater than a predetermined length, each subdivided voxel joining a finite number of voxel(s) of the voxelized 3D structural medical image.

18. The apparatus of claim 17, wherein the processor is further configured to iteratively subdivide by being configured to:
compute for each voxel of the 3D grid a bounding sphere,
compute for each EEG electrode sensor, a sphere being centered at the EEG electrode sensor and a radius being equal to the sensor detection distance,
determine, for each computed bounding sphere, whether the computed bounding sphere is intersecting with the computed spheres, and
for each voxel, subdivide the voxel when the respective computed bounding sphere is intersecting with one or more computed sphere while a size of the voxel is greater than the predetermined length, each subdivided voxel joining a finite number of voxels of the voxelized 3D structural medical image.

19. The apparatus of claim 17, wherein each voxel of the 3D grid having 2n voxels of the voxelized 3D structural medical image wherein $n \in \mathbb{N}$.

20. The apparatus of claim 17, wherein the processor is further configured to remove the voxels of the voxelized 3D structural medical image that are not enclosing a brain grey matter in the voxelized 3D structural medical image.

* * * * *